United States Patent [19]

Young

[11] Patent Number: 5,252,117
[45] Date of Patent: Oct. 12, 1993

[54] CELLULOSIC COMPOSITIONS

[75] Inventor: Donald C. Young, Fullerton, Calif.

[73] Assignee: Union Oil Company of California, Los Angeles, Calif.

[21] Appl. No.: 313,188

[22] Filed: Feb. 21, 1989

Related U.S. Application Data

[60] Division of Ser. No. 455,268, Jan. 3, 1983, Pat. No. 4,818,269, Continuation-in-part of Ser. No. 442,296, Nov. 17, 1982, abandoned, and Ser. No. 444,667, Nov. 26, 1982, abandoned, and Ser. No. 453,496, Dec. 27, 1982, Pat. No. 4,910,179.

[51] Int. Cl.$^5$ ............... C05F 11/00; C05C 9/00
[52] U.S. Cl. ................................ 71/23; 71/28; 127/34
[58] Field of Search ............... 71/23, 27, 28–30, 71/83; 127/34

[56] References Cited

U.S. PATENT DOCUMENTS

| | | | |
|---|---|---|---|
| Re. 1,995 | 6/1865 | Hoffman | 127/36 |
| 1,340,708 | 5/1920 | Fjellanger | 71/28 |
| 1,878,852 | 9/1932 | Hoppler et al. | 127/36 |
| 1,917,539 | 7/1933 | Miles | 127/37 |
| 1,919,623 | 7/1933 | Dreyfus | 127/37 |
| 2,767,108 | 10/1956 | Fetzer | 127/34 |
| 2,978,359 | 4/1961 | Wedell | 427/389 |
| 3,432,482 | 3/1969 | Ohfuka et al. | 526/220 |
| 3,558,530 | 1/1971 | Schroder et al. | 521/594 |
| 3,660,070 | 5/1972 | Maruta et al. | 536/47 |
| 3,778,431 | 12/1973 | Knightlinger et al. | 71/64.07 |
| 3,816,375 | 6/1974 | Bozer et al. | 536/47 |
| 3,873,734 | 3/1975 | Higgins et al. | 528/293 |
| 3,878,304 | 4/1975 | Moore | 426/69 |
| 3,918,952 | 11/1975 | Neumiller | 71/28 |
| 4,116,664 | 9/1978 | Jones | 71/29 |
| 4,214,888 | 7/1980 | Young | 71/28 |
| 4,310,343 | 1/1982 | Verdegaal et al. | 71/28 |
| 4,315,763 | 2/1982 | Stoller et al. | 71/29 |
| 4,397,675 | 8/1983 | Young | 71/28 |
| 4,402,852 | 9/1983 | Young | 252/183.13 |
| 4,404,116 | 9/1983 | Young | 252/183.13 |
| 4,439,348 | 3/1984 | Akerberg | 502/167 |
| 4,445,925 | 5/1984 | Young | 71/28 |
| 4,447,253 | 5/1984 | Young | 71/28 |
| 4,451,577 | 5/1984 | Coss | 502/167 |
| 4,474,925 | 10/1984 | Sartoretto et al. | 524/598 |
| 4,512,813 | 4/1985 | Young | 134/27 |
| 4,522,644 | 6/1985 | Young | 504/186 |
| 4,589,925 | 5/1986 | Young | 134/3 |
| 4,626,417 | 12/1986 | Young | 423/235 |
| 4,664,717 | 5/1987 | Young | 127/37 |
| 4,673,522 | 6/1987 | Young | 252/87 |
| 4,686,017 | 8/1987 | Young | 205/234 |
| 4,722,986 | 2/1988 | Young | 526/245 |
| 4,755,265 | 7/1988 | Young | 205/234 |

OTHER PUBLICATIONS

Science News, vol. 123, No. 23, Jun. 4, 1983, p. 366, "Cellulose Digestion by Lab Bacteria".
The Condensed Chemical Dictionary, 7th Edition, Van Nostrand Reinhold Co., New York, 1969, p. 908.

(List continued on next page.)

*Primary Examiner*—Ferris Lander
*Attorney, Agent, or Firm*—Michael H. Laird; Yale S. Finkle; Gregory F. Wirzbicki

[57] ABSTRACT

Cellulosic materials are physically and/or chemically modified by contact with a combination of urea and sulfuric acid in which at least 25 percent of the sulfuric acid is present as the monourea adduct of sulfuric acid. The cellulosic materials thus treated possess uniquely modified physical and chemical properties. The methods of the invention can be employed to weaken the physical structure of the cellulosic material and thereby to assist in clearing land of vegetation and vegetation residue and in compacting and other processing of waste cellulosic materials. The methods of the invention can also be employed to increase the food value of cellulosic materials for animals, including humans, and, in particular, to increase the food value of such materials for ruminant mammals. Novel cellulosic compositions suitable for use in the methods of this invention and novel compositions containing cellulosic materials which have been physically weakened, modified and/or which have improved food value, are also provided.

33 Claims, 1 Drawing Sheet

OTHER PUBLICATIONS

"Organic Chemistry of Bivalent Sulfur," Chemical Publishing Co., 1962, pp. 14, 15, 94 and 95.

"The Chemistry of Carboxylic Acids and Esters," Interscience Publishers, 1969, pp. 732, 733, 758 and 759.

D. F. duToit, Verslag Akad. Wetenschappen, 22, 573–4 (abstracted in Chemical Abstracts, 8, 2346; 1914).

L. H. Dalman, "Ternary Systems of Urea and Acid. I. Urea, Nitric Acid and Water. II. Urea, Sulfuric Acid and Water. III. Urea, Oxalic Acid and Water". JACS, 56, 549–53 (1934).

Sulfur Institute Bulletin, No. 10 (1964), "Adding Plant Nutrient Sulfur to Fertilizer".

Kirk–Othmer Encyclopedia of Chemical Technology, Third Edition, John Wiley and Sons, New York, 1980.

Jelks, "Treating Cellulosic Plant Matter," Chemical Abstract, 91:37800r (1979).

Bach et al., "Destroying Potato Plants," Chemical Abstract, 95:37118g (1981).

Adalla, Chemical Abstracts, 93:90069b (1980).

Kamilova, Chemical Abstracts, 93:63397a (1980).

Chan, Chemical Abstracts, 88)131876c (1978).

Title 40, Code of Federal Regulations, Part 180, Subpart D, Section 180.1019 (Jul. 1, 1980).

Young, U.S. Ser. No. 06/453,496 filed Dec. 27, 1982 for Acid Catalyzed Reactions and Compositions for Use Therein.

Young, U.S. Ser. No. 06/455,317, filed Jan. 3, 1983, for Plant Seed Compositions and Methods for Treating Plant Seeds.

Young, U.S. Ser. No. 06/673,508, filed Nov. 20, 1984, for Thermally Stable Urea-Sulfuric Acid Compositions and Methods of Manufacture.

Young, U.S. Ser. No. 06/688,689 filed Jan. 3, 1985, for Pesticidal Compositions and Methods for Controlling Pests.

Young, U.S. Ser. No. 06/783,368, filed Oct. 3, 1985, for Herbicidal Compositions.

Young, U.S. Ser. No. 06/822,285, filed Jan. 24, 1986, for Methods for Chemically Reducing Nitrogen Oxides.

Young, U.S. Ser. No. 06/918,546, filed Oct. 10, 1986, for Methods for Facilitating the Harvest of Food Crops.

Young, U.S. Ser. No. 07/009,829, filed Feb. 2, 1987, for Polysaccharide Compositions.

Young, U.S. Ser. No. 07/021,200, filed Mar. 3, 1987, for Electrolytic Cell.

Young, U.S. Ser. No. 07/050,530, filed May 13, 1987, for Methods for Removing Obstructions from Conduits.

Young, U.S. Ser. No. 07/116,472, filed Nov. 3, 1987, for Systemic Herbicides and Methods of Use.

Young, U.S. Ser. No. 07/149/424, filed Jan. 29, 1988, for Acid Catalyzed Reduction.

Young, U.S. Ser. No. 07/149,431, filed Jan. 29, 1988, for Friedel–Crafts Reactions.

Young, U.S. Ser. No. 07/149,701 filed Jan. 29, 1988, for Acid–Catalyzed Nitration.

Young, U.S. Ser. No. 07/149,734, filed Jan. 29, 1988, for Alkylation.

Young, U.S. Ser. No. 07/149,735, filed Jan. 29, 1988, for Methods for Acid–Catalyzed Reactions.

Young, U.S. Ser. No. 07/150,026, filed Jan. 29, 1988, for Isomerization.

Young, U.S. Ser. No. 07/150,076, filed Jan. 29, 1988, for Acid–Catalyzed Oxidative Reactions.

Young, U.S. Ser. No. 07/150,077, filed Jan. 29, 1988, for Demetallizing Organometallic Compounds.

Young, U.S. Ser. No. 07/150,079, filed Jan. 29, 1988, for Acid–Catalyzed Polymerization.

Young, U.S. Ser. No. 07/150,224, filed Jan. 29, 1988, for Esterification.

Young, U.S. Ser. No. 07/150,230, filed Jan. 29, 1988, for Acid–Catalyzed Reactions.

Young, U.S. Ser. No. 07/235,005, filed Aug. 22, 1988, for Vegetation Control.

Young, U.S. Ser. No. 07/235,799, filed Aug. 22, 1988, for Methods for Controlling Vegetation.

Young, U.S. Ser. No. 07/236,344, filed Aug. 22, 1988, for Systemic Herbicidal Compositions and Methods of Use.

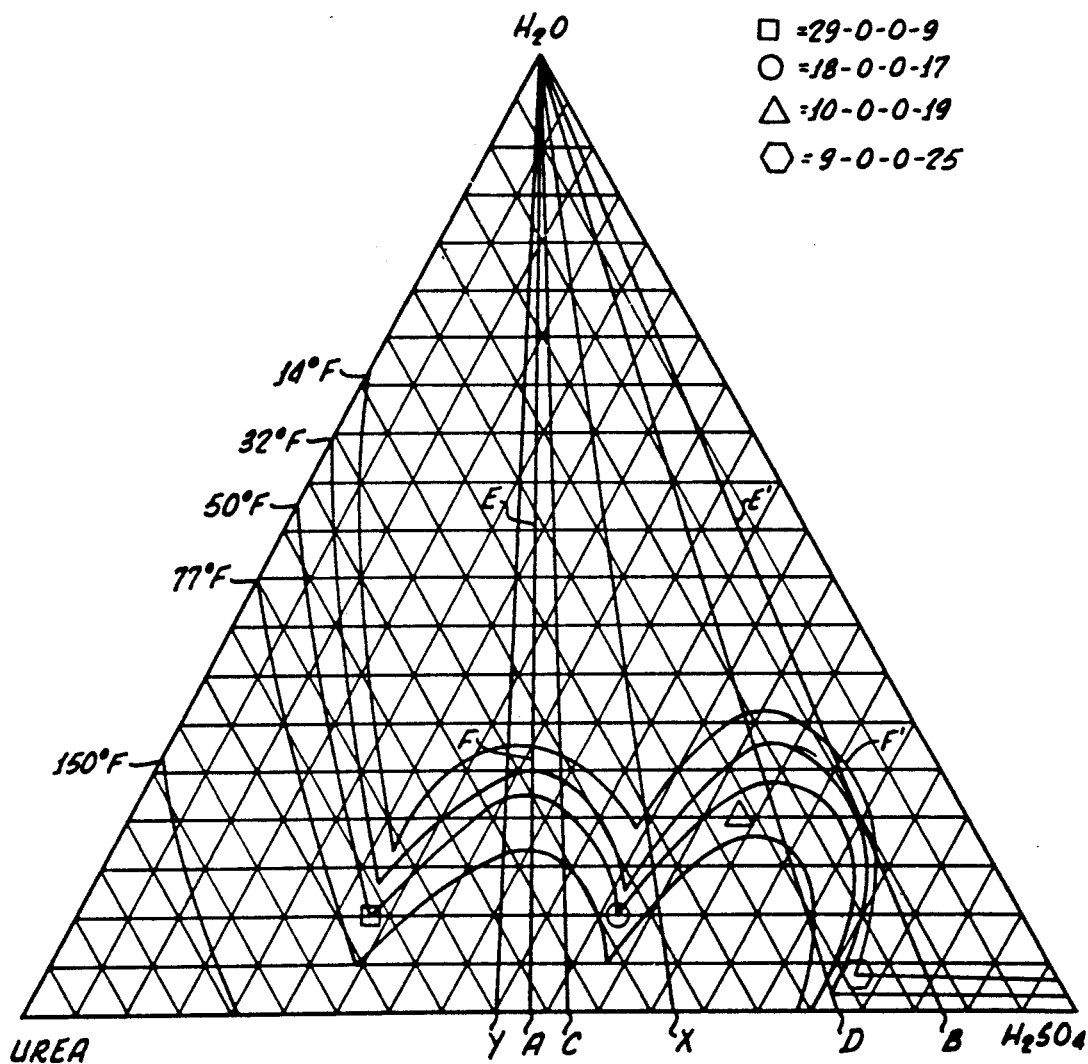

1

CELLULOSIC COMPOSITIONS

RELATED APPLICATIONS

This application is a division of copending application Ser. No. 06/455,268 filed Jan. 3, 1983, now U.S. Pat. No. 4,818,269, Apr. 4, 1989 which was a continuation-in-part of my copending applications, Ser. No. 442,296, SYSTEMIC HERBICIDAL COMPOSITIONS AND METHODS OF USE, filed Nov. 17, 1982, now abandoned, Ser. No. 444,667, METHODS FOR CONTROLLING VEGETATION, filed Nov. 26, 1982, now abandoned, and Ser. No. 06/453,496, ACID CATALYZED REACTIONS AND COMPOSITIONS FOR USE THEREIN, filed Dec. 27, 1982, now U.S. Pat. No. 4,910,179, Mar. 20, 1990.

BACKGROUND OF THE INVENTION

1. Field of the Invention

This invention relates to the field of cellulosic materials, and, in particular, it relates to methods of physically weakening and/or improving the food value of cellulosic materials, to cellulosic compositions useful in such methods, and to compositions containing modified cellulosic materials.

2. Description of the Art

Both urea and sulfuric acid are well known and are widely used in numerous industries for a variety of purposes, including fertilizers, soil adjuvants, chemical treating agents, chemical precursors, and reactants. The ability of sulfuric acid to catalyze a variety of organic reactions is also known. Urea and sulfuric acid are sometimes useful in combination, particularly in the agricultural industry when simultaneous addition of urea and sulfur to the soil is desired.

It is also known that urea and sulfuric acid will combine to form adducts including the monourea-sulfuric acid adduct and the diura-sulfuric acid adduct. For instance, D. F. du Toit, Verslag Akad. Wetenschappen, 22, 573-4 (abstracted in Chemical Abstracts, 8, 2346, 1914) disclosed the phase relationships between the solid phase and saturated solutions containing urea and sulfuric acid at 10° C. and 25° C. The Sulfur Institute, Sulfur Institute Bulletin No. 10 (1964), "Adding Plant Nutrient Sulfur to Fertilizer," disclosed that urea reacts with sulfuric acid to form two complexes of "urea sulfate" which are useful fertilizers. Methods of manufacturing certain combinations of urea and sulfuric acid are disclosed by Verdegaal et al. in U.S. Pat. No. 4,310,343 and by Jones in U.S. Pat. No. 4,116,664.

All animals including warm and cold-blooded animals, such as mammals, fish, birds, and reptiles, can derive at least some food value from cellulosic materials, particularly from cellulosic materials which contain vegetable protein. However, some animals, such as the ruminant mammals, can derive essentially all their food needs from cellulosic materials such as vegetation, notwithstanding the fact that contemporary methods of feeding domesticated ruminant animals usually involve the use of supplements, such as molasses, and other nitrogen sources, such as urea. Thus, while the food value of cellulosic materials can be important to essentially all animals, it is particularly important in the feeding of domesticated ruminant mammals.

Ruminant mammals are members of the suborder Ruminantia comprising even-toed hoofed mammals such as cattle, sheep, deer, camels and the like, which have complex three-or-four-chambered stomachs and the ability to derive nourishment from cellulosic feeds, in part, by virtue of the action of symbiont micro-organisms that assist the animal in breaking down the cellulosic structure. However, it is also known that ruminants have little, if any, ability to break down some more refractory cellulosic feeds such as rice stubble and wood fiber. Efforts to improve the food value of cellulosic materials, including the more refractory cellulosic materials, have been somewhat successful and have usually involved hydrolysis of the cellulosic materials with strong bases such as calcium, potassium and sodium hydroxides at relatively high temperatures, e.g., 300° F., and relatively long contact times. Reaction with lime (calcium hydroxide) is the most commonly studied procedure. However, these procedures are little used, if at all, due to the expense of reactant materials which are consumed during the process, the presence of significant base reaction products, e.g., calcium, potassium, or sodium salts, in the product, and processing costs, all of which make the product uncompetitive economically with known high nutrient value feeds such as alfalfa and grains.

The manufacture of certain commodities from cellulosic materials, such as the manufacture of paper from wood fiber, benefits by the physical weakening and partial breakdown of of the cellulosic structure. Such physical weakening of the cellulosic structure (which results from chemical interaction with one or more reagents) can be accomplished by any one of several methods. One of the most commonly used methods involves treatment with strong base such as calcium, potassium or sodium hydroxides at relatively high temperatures, pressures and contact times. The disposal of cellulosic wastes, such as waste paper, cardboard, wood particles, sawdust, and the like, can also benefit by reducing the bulk and increasing the compressibility of such materials by physically weakening the cellulosic structure of the waste material.

The problems involved in clearing or cultivating land containing significant amounts of brush, undergrowth or crop residue such as rice stubble, wheat stubble, crop vines, etc., after harvest, are very well known to the agricultural and land development industries. Weakening the physical structure of such cellulosic materials would markedly reduce the costs involved in plowing, clearing, harvesting, or otherwise handling such cellulosic materials. In situ treatment with strong base would be difficult if not impossible in most circumstances due to the high temperatures required to obtain realistic reaction rates and to the high cost of reactants that would be involved.

Sulfuric acid is effective for killing live vegetation and, in high enough dosages, will physically weaken the cellulosic structure of vines and other cellulosic materials through oxidation and charring. However, the dosage rates of sulfuric acid required to achieve any significant degree of physical structure weakening are substantial, and thus, they involve considerable expense. Furthermore, the hazards associated with the use of concentrated sulfuric acid are well known, and its application to in situ vegetation at rates required to significantly weaken vines and other vegetation can result in over-acidification of the soil and ecotoxic effects associated with excess acid runoff. Moreover, little, if any, benefit is realized by using concentrated sulfuric acid to modify the physical structure of cellulosic materials or increase the food value of such materials since sulfuric acid chars and destroys the cellulosic structure by oxidation. Thus, sulfuric acid diminishes rather than improves the quality of cellulosic materials to which it is applied.

While crop stubble and undergrowth can be controlled by burning, such practice results in considerable air-borne emissions and has been outlawed in several states. Other states such as Oregon that still allow burning charge for burning permits which make that alternative economically unattractive.

Obviously, waste cellulose can be disposed of as refuse or incinerated, while in situ vegetation, such as crop stubble, can be cleared or plowed under by mechanical means. However, the energy costs, time, and capital investment involved in such procedures are relatively high, and they often do not reclaim any potential value of the cellulosic material involved.

Accordingly, a need exists for improved methods of modifying cellulosic materials, for compositions useful in effecting the modifications of cellulosic materials, and for improved, modified, cellulosic compositions. In particular, a need exists for improved methods for (1) of physically weakening cellulosic materials, (2) chemically modifying cellulosic materials, and/or (3) improving the food value of cellulosic materials.

It is therefore one object of this invention to provide methods for modifying cellulosic materials.

It is another object to provide methods for weakening the physical structure of cellulosic materials without charring the cellulose content thereof.

Another object is the provision of modified cellulosic materials.

Another object is the provision of cellulosic materials having weakened physical structure and reduced resistance to deformation and shear.

Another object is the provision of improved methods for reducing the physical strength of in situ crop residues such as crop stubble.

Another object is the provision of improved methods for clearing agricultural fields and/or fields containing indigenous vegetation.

Another object is the provision of methods for improving the food value of cellulosic materials.

Another object of this invention is the provision of methods for improving the food value of ruminant fees.

Yet another object of this invention is the provision of novel compositions useful in the production of modified cellulosic materials.

Other objects, aspects and advantages of this invention will be apparent to one skilled in the art in view of the following disclosure, the drawing and the appended claims.

SUMMARY OF THE INVENTION

Briefly, the invention provides novel (1) methods of modifying cellulosic materials, (2) methods of weakening the physical structure of cellulosic materials, (3) methods of chemically modifying cellulosic materials for use as chemical precursors or in the manufacture of cellulose-containing commodities, (4) methods of improving the food value of cellulosic materials, (5) cellulosic compositions useful in such methods, and (6) cellulosic compositions having reduced physical strength and/or improved value as foods and/or as components of cellulose-containing commodities.

The methods of this invention involve the modification of cellulosic materials by contacting such materials with the monourea adduct of sulfuric acid. The cellulosic materials are usually contacted with a urea-sulfuric acid component which contains the reaction product of urea and sulfuric acid and in which the urea-sulfuric acid molar ratio is within the range of about $\frac{1}{4}$ to about 7/4 so that at least about 25 percent of the sulfuric acid is present as the monourea adduct of sulfuric acid. The urea-sulfuric acid component is usually contacted with the cellulosic material in the form of an aqueous solution, which solution may optionally contain a surfactant. These methods are particularly suitable for chemically modifying and/or for weakening the physical structure of cellulosic materials, and for improving the food value of cellulosic materials, particularly for ruminant mammals.

The novel compositions of this invention involve mixtures of cellulosic materials and the urea-sulfuric acid components useful in the methods of this invention, and they may optionally contain a surfactant. The novel compositions also involve cellulosic materials produced by contacting cellulosic materials with the urea-sulfuric acid components of this invention, which compositions are chemically modified, physically weakened, and/or which have improved food value.

The methods and compositions of this invention minimize or eliminate many of the deficiencies associated with current practices. These methods and compositions can be employed to chemically modify, physically weaken and/or improve the food value and digestibility of cellulosic materials for all types of animals. The urea-sulfuric acid components useful in this invention result only in the addition of nutrients such as nitrogen and sulfur to the environment or to the treated cellulosic materials. They do not introduce toxic materials into either the environment or treated cellulosic materials. Unlike sulfuric acid, the methods and compositions of this invention do not destroy the value of cellulosic materials either as foods or as raw materials for the manufacture of cellulosic commodities. The urea-sulfuric acid components useful in this invention are much more active for the conversion of cellulosic materials than is sulfuric acid. Thus, methods which employ the urea-sulfuric acid components herein are more effective and economical than methods involving the use of sulfuric acid alone. When employed to treat vegetation in place on the soil surface, the methods of this invention result not only in physical weakening of the in situ vegetation, but they also accelerate the decomposition of the vegetable matter, possibly by facilitating bacterial and enzymatic action. Thus, they accelerate the return of nutrients contained in the vegetation to the soil.

BRIEF DESCRIPTION OF THE DRAWING

This invention will be more readily understood by reference to the drawing which is a ternary-phase diagram for the urea, sulfuric acid, and water system illustrating isotherms at several different temperatures, the existence of three prominent eutectics along those isotherms, and the compositions of the urea-sulfuric acid components useful in the methods and compositions of this invention.

DETAILED DESCRIPTION OF THE INVENTION

This invention provides novel methods for modifying cellulosic materials which involve contacting the cellulosic materials with a urea-sulfuric acid component, which contains the monourea adduct of sulfuric acid. In particular, the methods of this invention are employed to (1) physically weaken cellulosic materials, (2) convert cellulosic materials to compositions useful in the manufacture of cellulose-containing articles of manufacture or chemical compositions derived from cellulosic materials, (3) improve the food value of cellulosic materials particularly for ruminant mammals, and (4) treat in situ vegetation to facilitate cultivation or land clearing and accelerate the decomposition of such in situ vegetation and the return of its nutrient value to the soil. This invention also provides novel mixtures of cellulosic materials urea, and sulfuric acid, which are useful in the methods of this invention, as well as novel compositions which result from the treatment of cellulosic materials with the urea-sulfuric acid components useful in the methods of this invention.

Any cellulosic material can be chemically and/or physically modified by treatment in accordance with the methods of this invention. Illustrative cellulosic materials are in situ vegetation or vegetation residue located on the soil surface, and accumulated (gathered) cellulosic materials such as animal foods, cellulosic wastes, agricultural crop wastes, weeds, etc. Illustrative of insitu and accumulated agricultural wastes and vegetation are living or dead crop and weed stubble, foliage, vines, brush, and the like. Illustrative of crop stubble which can be treated either in situ on the soil surface or after accumulation, are rice stubble, wheat stubble, and the residue remaining after the harvesting of corn, barley, rye, and grass seed crops. The treatment of these and similar crop residues in accordance with this invention is advantageous since a large portion of the vegetation of such crops is left as residue on the soil surface, and the removal or physical weakening of such residue facilitates subsequent land use. Illustrative of vines that can be physically weakened to enable more expedient land management include crop vines such as grapes, berries of all varieties, potato, tomato, sugar beets, melons, squash (including pumpkins), and the like, and indigenous weed vines such as wild blackberry, poison ivy, poison oak, etc. Illustrative accumulated industrial or household cellulosic wastes include newspapers, craft paper (cardboard), wood scrap, sawdust, waste cotton, harvested vegetation residue, e.g., stems, stalks, vines, and the residue from processing foods such as vegetables, fruits, grains, etc., including fruit peels, vegetables, and fruit pulp, potato peels, wheat chaff, and the like.

The treatment of such accumulated cellulosic wastes by the methods herein physically weakens the cellulosic structure thereby producing a material which is more compressible and more easily sheared. Thus, the waste can be more easily compacted and handled by conventional means. Furthermore, the chemical modification of such cellulosic materials in accordance with the methods of this invention results in the formation of a treated cellulosic material that is more susceptible to subsequent chemical treatment or processing, such as in the manufacture of paper, cardboard, particle board, and other cellulose-derived compositions and articles of manufacture.

The food value of any cellulosic material for all animals can be improved by the methods of this invention. Thus, any of the in situ or accumulated cellulosic material referred to above can be treated to improve its food value for animals. This is particularly true of ruminant mammal foods. Thus, ruminant feeds of acceptable food value can be produced from in situ or accumulated cellulosic materials of little or no ruminant food value by treatment in accordance with this invention. Such cellulosic materials include crop stubble and indigenous vegetation, wood fiber, and other cellulosic wastes, such as paper and the like. Furthermore, the food value of more conventional animal foods, including foods for humans, ruminants, and other animals including birds and fish, can be improved by treatment in accordance with the methods of this invention. Thus, cellulosic materials, such as raw or processed grains, vegetables, fruits, grass crops and the like, can be treated by the methods of this invention to improve their food value.

The management and harvesting of tuberous crops is also benefited by the use of the methods of this invention. Illustrative of such tuberous crops are potatoes, beets (including sugar beets), turnips, and other tubers. Topical application of the urea-sulfuric acid component in accordance with this invention to the tuber foliage chemically and physically modifies the foliage and tuber vines, when present, and thereby facilitates harvesting and land clearing or cultivating. Such treatment in accordance with this invention also promotes tuber set by inducing senesence and associated benefits such as skin thickening on potatoes.

Without intending to limit the scope of this invention to any particular theory, many of the advantages associated with the methods and compositions of this invention involve the ability of the urea-sulfuric acid components employed in the methods of this invention to catalyze the hydrolysis of cellulose. That catalytic ability accounts for at least part of the herbicidal activity of the described urea-sulfuric acid components which is discussed in more detail in my copending application Ser. No. 444,667 filed Nov. 26, 1982, the disclosure of which is incorporated herein by reference. As described herein, the urea-sulfuric acid components are capable of effecting the conversion of cellulosic materials other than living and dead plant matter as well.

The urea-sulfuric acid components employed in the compositions and methods of this invention are reaction products of urea and sulfuric acid containing the monourea adduct of sulfuric acid. The urea-sulfuric acid components usually have urea-sulfuric acid molar ratios within the range of about $\frac{1}{4}$ to about 7/4 so that at least about 25 percent of the sulfuric acid is present as the monourea adduct of sulfuric acid. The urea-sulfuric acid components may be employed either as solids or as aqueous solutions.

The composition of the urea-sulfuric acid components useful in the compositions and methods of this invention can be conveniently expressed in terms of 4-digit designations such as 18-0-0-17 which are conventionally used in the agricultural industry to designate the concentration of nitrogen, phosphorus (as $P_2O_5$), potassium (as $K_2O$), and a fourth component (in this case sulfur expressed as the element). Thus, the composition 18-0-0-17 contains 18 weight percent nitrogen derived from urea and 17 weight percent sulfur derived from sulfuric acid. Using the atomic weights for nitrogen (14.01) and sulfur (32.07) and the molecular formulas and molecular weights for urea (60.06) and sulfuric acid (98.08), it can be determined that this composition contains 38.6 weight percent urea and 52.1 weight percent sulfuric acid. By difference, the composition contains 9.3 weight percent water. The concentrations of sulfuric acid and urea in all other compositions can be determined by the same procedure.

The compositions and some crystallization temperatures of urea-sulfuric acid solutions useful in the methods and compositions of this invention are illustrated in the ternary phase diagram of the drawing. The phase diagram defines the relative proportions in weight percent for each of the three components—urea, sulfuric acid, and water—at any point within the diagram. At each apex of the triangle the system consists completely of the indicated component. Thus, the concentration of urea at the urea apex is 100 percent and diminishes linearly to 0 along a straight line from the urea apex to the $H_2O$-$HSO_4$ boundary line, i.e., the side of the triangle opposite the urea apex. The same is true of the remaining two components: water and sulfuric acid.

The diagram also illustrates the isotherms for the system at 14° F., 32° F., 50° F., 77° F., and 150° F. The 150° F. isotherm is illustrated only partially at the lower left-hand portion of the diagram. Each isotherm defines liquid compositions which, if cooled below the temperature indicated for the respective isotherm, will precipitate components of the system. However, the solutions will super-cool dramatically, e.g., by as much as 50° F., or more, under quiescent conditions in the absence of seed crystals, impurities, etc., that promote crystallization.

As indicated by the pattern of the isotherms, systems having a fixed ratio of urea to sulfuric acid become more stable at lower temperatures as the water concentration is increased. This is true throughout most of the phase diagram with the exception of the region in the vicinity of the higher acid eutectic in the lower right-hand portion of the phase diagram.

Three prominent eutectics are apparent within the region of the illustrated isotherms. Each eutectic represents a discontinuity in the response of the system, e.g., of crystallization point, to changes in solute concentration, and indicates the points of maximum solute concentration for a given isotherm in the regions of the phase diagram associated with those eutectics.

As indicated in the legend on the drawing, the left-hand eutectic on the 50° F. isotherm corresponds to the formulation 29-0-0-9. The middle eutectic on the same isotherm corresponds to the composition 18-0-0-17. The right-hand eutectic on the 14° F. isotherm corresponds to 9-0-0-25, and the formulation intermediate the 50° F. and the 77° F. isotherms between the middle and right-hand eutectics indicated by a triangular designation corresponds to 10-0-0-19.

The bold horizontal lines E—E′ and F—F′ within the diagram prescribe the boundaries of concentrated urea-sulfuric acid compositions that are preferable from the standpoint of manufacture and packaging prior to dilution for use.

Compositions falling below line E—E′ have solute, i.e., urea and sulfuric acid, concentrations of 50 weight percent or higher. Compositions falling below line F—F′ located at the 25 percent water line, contain 75 weight percent of a combination of urea and sulfuric acid, or more. It can be readily seen that the four specific compositions designated in the diagram contain more than 75 weight percent solute.

Bold lines running between the urea sulfuric acid boundary (the lower boundary of the diagram) and the water apex generally prescribe the operable and preferred urea-sulfuric acid component compositions employed in this invention. Line Y defines compositions having a 2/1 urea/sulfuric acid molar ratio. This line intersects the urea-sulfuric acid boundary at a point corresponding to approximately 55.0 weight percent urea. Compositions falling to the left of line Y do not contain any amount of the monourea-sulfuric acid adduct; they consist of combinations of the diurea adduct and excess urea. Such compositions have little or no ability to modify cellulosic materials, at least not in comparison to the monourea adduct. Compositions falling to the right of line Y contain at least some of the monourea adduct, and the concentration of that adduct increases as the composition approaches line X. Compositions falling on line X have urea/$H_2SO_4$ molar ratios of 1/1 and correspond to those in which both the urea and sulfuric acid are present only as the monourea-sulfuric acid adduct. Line X intersects the urea-$H_2SO_4$ boundary at a urea concentration of 38.0 weight percent.

Compositions falling between lines A and B are those in which at least 25 percent of the sulfuric acid is present as the monourea-sulfuric acid adduct. In compositions falling on line A, 25 percent of the sulfuric acid is present as the monurea adduct and 75 percent is present as the diurea-sulfuric acid adduct. In compositions falling along line B, 25 percent of the sulfuric acid is present in the monurea adduct and 75 percent is present as free sulfuric acid. Line A intersects the urea-sulfuric acid boundary at a point corresponding to 51.9 weight percent urea; line B intersects the same boundary at the 13.2 weight percent urea level.

In compositions falling between lines C and D, at least 50 percent of the sulfuric acid is present as the monourea adduct. Line C defines compositions in which 50 percent of the sulfuric acid is present as the monourea adduct and 50 percent is present as the diurea-sulfuric acid adduct. Compositions falling on line D correspond to those in which 50 percent of the sulfuric acid is uncomplexed (free) sulfuric acid. Lines C and D intersect the urea-sulfuric acid boundary at points corresponding to 47.9 and 23.4 weight percent urea, respectively.

The urea-sulfuric acid component can be produced by either batch or continuous processes by the reaction of urea and sulfuric acid and, optionally, water. The urea-sulfuric acid component is preferably substantially or completely free of decomposition products of urea and/or sulfuric acid, such as sulfamic acid, ammonium sulfamate, ammonium sulfate. etc., to assure that the preferred liquid and solid urea-sulfuric acid components employed in the methods and compositions of this invention are also free of such decomposition products. The absence of decomposition products in the urea-sulfuric acid component also assures that the sulfuric acid activity of that component has not been degraded by decomposition. Decomposition of the sulfuric acid decreases the amount of acid in the urea-sulfuric acid component available to combine with the urea to form the active monourea-sulfuric acid adduct. Urea-sulfuric acid components free of decomposition products can be produced by the reaction of urea and concentrated sulfuric acid by the methods described in my copending application Ser. No. 318,629, filed Nov. 5, 1981, now U.S. Pat. No. 4,445,925 the disclosure of which is incorporated herein by reference.

The monourea adduct of sulfuric acid is by far the most active combination of urea and sulfuric acid for use in this invention. The diurea sulfuric acid adduct exhibits little if any ability to modify cellulose either chemically or physically. Although uncomplexed sulfuric acid rapidly attacks cellulosic materials, it does so primarily by oxidation and sulfonation, and in doing so, it is consumed by conversion to sulfates and similar reaction products. The reaction of sulfuric acid and cellulosic materials also results in the destruction of the cellulosic material. Accordingly, the most preferred compositions are those in which essentially all of the urea and sulfuric acid are present as the monourea-sulfuric acid adduct. Such compositions have a urea/sulfuric acid molar ratio of 1/1. Compositions containing substantial amounts of either the diurea adduct or free sulfuric acid can be employed although they are not as active as the compositions having urea/sulfuric acid molar ratios of 1/1 in the methods of this invention. Thus, the preferred solid and aqueous urea-sulfuric acid components are those in which at least about 75, usually at least about 85, and most preferably at least about 90 percent of the sulfuric acid is present as the mono- and/or diurea-sulfuric acid adduct. Particularly preferred compositions are those that contain essentially no free sulfuric acid; thus, essentially 100 percent of the sulfuric acid would be combined with urea as the mono- and/or diurea adduct. Furthermore, since the monourea adduct is the most active combined form of urea and sulfuric acid, at least about 25, usually at least about 50, preferably at least about 70, and most preferably about 80 to about 100 percent of the sulfuric acid is present as the monourea-sulfuric acid adduct.

The monourea-sulfuric acid adduct can be employed to modify cellulose even in very dilute aqueous solutions. For instance, the 17-0-0-17 composition which contains about 85 weight percent urea and sulfuric acid on a combined weight basis, as produced, can be diluted by as much as 200 to 1 with water to produce a dilute, aqueous urea-sulfuric acid component containing less than 0.5 weight percent solute useful in the compositions and methods of this invention. Even higher dilution ratios can be employed but are not preferred due to the difficulty involved in applying a sufficient amount of the active monourea adduct to the treated cellulosic material.

Although the monourea adduct appears to dissociate to urea and sulfuric acid in solutions containing significantly less than about 0.5 weight percent combined urea and sulfuric acid, the dissociated components will recombine to form the active adduct on the treated cellulosic material upon evaporation of water from the solution.

Very low monourea adduct concentrations, e.g., 0.2 percent, or less, do not usually allow for sufficient dosage rates of the urea-sulfuric acid component in many instances. Thus, the applied solutions will usually contain at least about 0.5, generally at least about 1, preferably at least about 5, and most preferably at least about 10 weight percent urea and sulfuric acid based on the combined weight of those two components. The concentrated solutions, e.g., those in which the urea and sulfuric acid, in combination, constitute 75 percent or more of the aqueous solution, can also be employed directly for the modification of cellulosic materials. However, more dilute solutions, which have lower viscosities, facilitate more even distribution of the urea-sulfuric acid component, particularly when a relatively low dosage of that component is applied to a large volume of cellulosic material.

With these factors in mind, the liquid urea-sulfuric acid components contacted with the cellulosic material will usually contain about 0.5 to about 90, normally about 1 to about 90, and preferably about 5 to about 80 weight percent urea and sulfuric acid on a combined weight basis.

The useful and preferred concentrations of urea and sulfuric acid, and of the mono- and diurea adducts relative to each other, can also be expressed in terms of the urea/sulfuric acid molar ratio. This ratio will be the same in the solid compositions useful in this invention as it is in aqueous solutions made either directly or by dissolving those solid compositions in water, and will usually be within the range of about $\frac{1}{4}$ to about 7/4, preferably about $\frac{1}{2}$ to about 3/2, and most preferably about 1/1 to about 3/2. Urea/sulfuric acid molar ratios within the range of about 1/1 to about 3/2 define compositions containing essentially no uncomplexed sulfuric acid in which at least 50 percent of the sulfuric acid is present as the monourea-sulfuric acid adduct.

A composition having a urea/sulfuric acid molar ratio of 3/2 contains 3 moles of urea for every 2 moles of sulfuric acid. Assuming complete reaction between the urea and sulfuric acid (which is essentially always the case), 50 percent of the sulfuric acid is present as the diurea-sulfuric acid adduct and 50 percent is present as the monourea adduct. Similarly, in a composition having a urea/sulfuric acid ratio of $\frac{1}{2}$, 50 percent of the sulfuric acid is present as the monourea-sulfuric acid adduct and 50 percent is unreacted "free" acid.

The urea-sulfuric acid components employed in the methods and compositions of this invention may also contain one or more surfactants, which surfactants are preferably chemically stable in the urea-sulfuric acid component. Surfactants accentuate the ability of the urea-sulfuric acid components to modify essentially all types of cellulosic materials and broaden the scope of cellulosic materials that can be modified by the methods of this invention. In particular, surfactants increase the activity of the urea-sulfuric acid components toward cellulosic materials which contain a significant amount of non-cellulosic substances which are not readily wet by the aqueous urea-sulfuric acid components which do not contain surfactants. Thus, surfactants accentuate the activity of the urea-sulfuric acid components toward cellulosic materials that are coated with or contain significant amounts of lipophilic substances such as the waxy cuticle on the foliage and stems of many forms of vegetation, lignins and oils contained in wood and other vegetation, and the like.

The surfactants employed in the urea-sulfuric acid component are preferably sufficiently chemically stable in the urea-sulfuric acid component to assure that the surfactant retains its wetting ability for the period of time required to manufacture, store, transport, and/or apply the compositions. The stability of any surfactant can be readily determined by adding an amount of the surfactant to the urea-sulfuric acid component in which it is to be employed and monitoring the combination by conventional nuclear magnetic resonance (NMR) techniques. NMR can be used to monitor the frequency and magnitude of spectral peaks characteristic of a selected nucleus, e.g., a hydrogen nucleus, in the subject molecule, i.e., in the surfactant. Persistent spectral peak magnitude and frequency over a period of 5 to 6 hours indicate stability. Diminished magnitude or a shift in peak frequency associated with the selected nucleus indicates instability, i.e., that the arrangement of functional groups in the surfactant molecule has been modified.

Illustrative of classes of stable surfactants are nonionics such as the alkylphenol polyethylene oxides, anionics such as the long chain alkyl sulfates, and cationics such as 1-hydroxyethyl-2-heptadecenyl gloxalidin. Of these, the polyethylene oxide nonionic surfactants are particularly preferred. Illustrative of preferred specific surfactants is the nonionic surfactant marketed by Thompson-Hayward, Inc., under the trademark T-MULZ 891.

The concentration of surfactant employed in the urea-sulfuric acid component is preferably sufficient to increase the wetting ability of that component for the cellulosic material to be treated. Surfactant concentration will usually be at least about 0.05, generally at least about 0.1, and preferably at least about 0.2 weight percent of the aqueous solution as applied. Surfactant concentrations of about 0.2 to about 1 weight percent are adequate in most applications. The concentration of surfactant in the solid compositions employed in one embodiment of this invention should be sufficient to produce the desired concentration in the aqueous solution that is to be produced by dissolving the solid in water. For example, a solid urea-sulfuric acid composition that is to be mixed with sufficient water in contact with the treated cellulosic material to produce an aqueous solution containing 5 weight percent of a combination of urea and sulfuric acid would be diluted by a factor of 19 to 1. Thus, the solid composition should contain approximately 19 times the surfactant concentration desired in the solution on a weight percent basis. Hence, if a final solution surfactant concentration of 0.1 weight percent is desired, the solid composition should contain approximately 1.9 weight percent of that component.

The solid and liquid urea-sulfuric acid components employed in this invention may also contain one or more other additives, components or adjuvants that complement or assist in the modification of the cellulosic material to be treated. Thus, they may contain polar solvents that facilitate extraction of extractable constituents from the cellulosic material. Similarly, urea-sulfuric acid components employed to treat in situ vegetation may contain one or more of the known major and micro nutrients and/or soil adjuvants such as phosphorus (from phosphoric acid), magnesium, manganese, potassium, zinc, boron, etc., derived from the respective oxides, hydroxides, sulfates, nitrates, and the like.

Taking all of the foregoing factors into account, the aqueous urea-sulfuric acid components will usually contain about 0.5 to about 90, generally about 1 to about 90, and preferably about 5 to about 80 weight percent of the combination of urea and sulfuric acid (on a dry-weight basis); and, optionally, at least about 0.5, generally at least about 0.1, and preferably at least about 0.2 weight percent of one or more surfactants.

The solid urea-sulfuric acid components employed in this invention usually contain at least about 50, and preferably at least about 80 weight percent of the combination of urea and sulfuric acid. The solids will usually contain at least about 20, generally at least about 50, preferably at least about 80 weight percent of the preferred monourea-sulfuric acid adduct. They may optionally contain sufficient amounts of the optional surfactant component to assure the presence of an effective concentration of that component in aqueous solutions produced by dissolving the solid compositions in water.

The solid compositions employed in this invention containing one or more surfactants (when desired), and/or additional adjuvants, can be obtained by crystallizing them from their respective aqueous solutions. The surfactant and/or adjuvant, when present, will either crystallize at approximately the same temperature or will be entrained with the crystallized urea-sulfuric acid component. In the alternative, the surfactant and/or adjuvant, can be added to the dried or damp urea-sulfuric acid component by any suitable mixing technique after crystallization of the urea-sulfuric acid component from solution.

The 18-0-0-17 composition crystallizes at 50° F. The 10-0-0-19 composition crystallizes at about 42° F., and the 9-0-0-25 composition crystallizes at 14° F., as indicated by the crystallization curves in the drawing. Crystallization points for other compositions can be determined from the drawing or by cooling the selected solution until crystallization occurs. The optional surfactant component usually will not significantly affect the crystallization point at most concentrations employed. The crystallized material can be separated from the supernatant aqueous phase by filtration or by decanting excess liquid, and drying.

Substantially anhydrous solid compositions can be obtained by washing the dried, crystallized urea-sulfuric acid component with a strongly hydrophillic solvent such as absolute ethanol or acetone. Ten to 100 weight parts solvent per weight part solute are usually adequate for this purpose.

The monourea adduct-containing component is stable at ambient conditions and has negligible vapor pressure up to its decomposition temperatures of about 300° F. in the absence of water. Decomposition temperatures of the anhydrous solids do not change significantly with composition. However, urea-sulfuric acid components decompose almost explosively at much lower temperatures, e.g., 176° F. and below, in the presence of water. The most preferred solid composition consisting of the 1/1 urea/sulfuric acid molar adduct has a melting point of about 100° F., and the melting point of the urea-sulfuric acid component increases as the urea/acid ratio deviates from 1:1 in either direction in a manner paralleling the crystallization curves shown in the drawing.

The aqueous solutions of the urea-sulfuric acid components employed in the methods and compositions of this invention can be produced by any method capable of producing a solution of the desired composition. Thus, the surfactant and/or other components, when used, can be added to the concentrated urea-sulfuric acid solution during or immediately after its manufacture by the process described in my copending application Ser. No. 318,624, referred to above, or they can be added to the urea-sulfuric acid component prior to its application to the cellulosic material to be treated. Alternatively, the optional components can be mixed with the amount of water required to produce a concentrated or dilute aqueous solution, as desired, before or concurrently with the solid or concentrated aqueous urea-sulfuric acid component. Of course, dissolution of the solid compositions of this invention that contain both the urea-sulfuric acid component and the desired optional components, in water, will also result in formation of the desired aqueous solution. The liquid urea-sulfuric acid components useful in the methods and compositions of this invention can also be formed in situ by mixing a solid urea-sulfuric acid component with water while in contact with the cellulosic material to be treated.

In accordance with the methods of this invention, the cellulosic material to be treated is contacted with the urea-sulfuric acid components useful in the methods of this invention at dosage rates and under conditions sufficient to chemically and/or physically modify the cellulosic material. These methods are particularly useful for physically weakening cellulosic materials and for improving the food value of cellulosic materials for all types of animals, particularly for ruminant mammals. The ability of the methods of this invention to physically weaken cellulosic material is particularly useful in the clearing of land containing vegetation or undergrowth and in the cultivation of cultivated fields containing plant residues, particularly fields containing plant residues that are difficult to manage, such as crop vines and the residues of grain crops such as rice, wheat and the like. They are also useful for the elimination of vines associated with annual vine crops, for the pre-harvest treatment of tuberous plants to assist in harvesting and to promote fruit set, and for the conversion of cellulosic materials to cellulose-containing compositions for producing articles of manufacture, particularly for the manufacture of paper articles, particle board and the like.

The urea-sulfuric acid component can be contacted with the cellulosic material to be treated by any procedure capable of effecting adequate distribution of the urea-sulfuric acid component throughout the cellulosic material. Illustrative contacting procedures include spraying the cellulosic material with or immersing it in the liquid urea-sulfuric acid component, dusting or otherwise distributing the solid urea-sulfuric acid component onto the cellulosic material and then mixing the solid component with water while in contact with the cellulosic material, and other procedures of liquid-solid and solid-solid contacting known in the art.

The urea-sulfuric acid component should be applied to the cellulosic material at a dosage rate sufficient to physically weaken the cellulosic material when that objective is desired. For instance, it is often desirable to physically weaken reclaimed paper, paperboard, and wood products prior to further processing, and to physically weaken crop stubble, vines, underbrush, and the like in cultivated fields prior to cultivation or on uncleared land prior to clearing.

In another embodiment of this invention, the urea-sulfuric acid component can be contacted with the cellulosic material at a dosage rate and under conditions of time and temperature sufficient to increase the food value of the cellulosic material for animals. Animal feeds that can be treated and/or produced in accordance with this method embodiment of the invention include foods for mammals including humans and particularly ruminant mammals such as cattle, deer, sheep, and the like, fish, domestic and wild foul such as chickens, ducks, turkeys, etc., and reptiles. The cellulosic material treated to improve food value will often, but need not necessarily contain vegetable protein, and the methods of this invention also improve the digestibility of the protein in the treated cellulosic material.

Dosage rates of the urea-sulfuric acid components useful in the methods of this invention sufficient to effect the modifications of cellulosic materials referred to above will usually correspond to at least about 0.1 weight percent of the combination of urea and sulfuric acid based on the weight of cellulosic material. Ordinarily, however, the urea-sulfuric acid components will be applied to the cellulosic material at dosage rates at least about 1 pound, preferably at least about 2 pounds of the urea-sulfuric acid component (on a water-free basis) per 100 pounds of cellulosic material, particularly when it is desirable to significantly weaken the cellulosic material. Somewhat lower dosage rates of at least about 1 pound of the urea-sulfuric acid component per 1,000 pounds of cellulosic material can be employed to increase the food value of the cellulosic material provided that the resulting mixture is allowed to react for a sufficient period of time. Cellulosic materials can be modified at even faster rates, and higher degrees of conversion can be achieved, by the use of even higher dosage rates of up to 5, and even up to 10 pounds of the urea-sulfuric acid component per 100 pounds of cellulosic material. Thus, the rate and degree of physicaly weakening and/or food value improvement of cellulosic materials can be increased by using such higher dosages of the urea-sulfuric acid components.

Dosage rates are more conveniently expressed in terms of pounds per acre when the urea-sulfuric acid components are applied to in situ vegetation on the soil surface. Such dosage rates usually correspond to at least about 50 and preferably at least about 100 pounds of the urea-sulfuric acid component per acre (water-free basis), which dosage rates are usually sufficient to physically weaken and increase the food value of the in situ vegetation thus contacted.

Cellulosic materials can be modified in accordance with the methods of this invention under ambient conditions although temperatures of at least 32° F. are generally required to obtain any significant rate of modification. Temperatures within the range of about 50° to about 160° F. are usually preferred. The temperature should be maintained below the thermal decomposition temperature of the urea-sulfuric acid component, i.e., below about 176° F. The rate at which cellulosic materials are modified by the methods of this invention increases as temperature is increased; thus, higher conversion rates and more complete conversions can be achieved at temperatures above 80° F. and particularly at temperatures within the range of about 100° to about 160° F.

The conversion of the cellulosic material commences almost immediately upon contact of the cellulosic material with the urea-sulfuric acid component. However, significant modification of the cellulosic material will usually not be observed in less than about 10 minutes of contact time except at high temperature and high dosage rates of the urea-sulfuric acid component. Longer contact times of 24 hours or more are generally required for significant conversions of relatively large particles of refractory cellulosic materials such as wood chips.

Optimum dosage rates of the urea-sulfuric acid component, surfactant concentrations, reaction temperature, and contact times required to achieve the desired degree of chemical modification, physical weakening, and/or food value improvement, will differ depending on the characteristics of the cellulosic material to be treated and on the extent of modification desired. Contacting conditions best suited for any particular conversion can be determined by contacting the cellulosic material with urea-sulfuric acid components of different composition at different dosage rates and at several different temperatures and contact times, and determining the extent of modification obtained in each case.

The following specific applications illustrate treatment conditions suitable for several types of cellulose modifications which can be achieved by the methods of this invention. In situ rice stubble cannot be easily broken from the roots and cannot be removed without pulling the roots from the ground. Such stubble is usually dense and matted and is firmly attached to an extensive root structure. The postharvest stubble of other grain crops is similar to rice stubble in these respects, and the cultivation or clearing of fields containing such stubble requires the expenditure of substantial amounts of mechanical energy. However, after treatment at a dosage rate equivalent to 30 gallons per acre of 17-0-0-17 at approximately 60° F. for two days, rice stubble can be easily crumbled to powder by hand. Similar effects can be achieved with other types of crop stubble. The physical strength of cardboard, waste paper, wood chips, cotton and other cellulosic materials can also be significantly reduced by treatment with the urea-sulfuric acid components in accordance with this invention. The occurrence of significant physical weakening is readily confirmed by compressing the material either by hand or by any one of several varieties of calibrated compression or compacting force-testing instruments.

Significant improvement in food value can be achieved within the time frames referred to above, and the extent of such improvement can be determined by digestibility tests known to the food processing industries. For instance, the degree of improvement of ruminant food value can be determined by procedures known to the animal husbandry industry, such as the artificial ruminant study which involves the determination of invitro dry matter disappearance (IVDMD). The invitro dry matter disappearance test involves the innoculation of a standard nutrient broth containing the selected ruminant feed with rumen microorganisms at standard pH and temperature for about 12 to 16 hours and determining, by filtration and drying, the amount of dry matter remaining in the digested mixture. Comparison of that value to the amount of dry matter added to the nutrient broth establishes the amount of the test feed that has been digested. Similar tests are available for determining the food value of human foods, and the results of such tests can be employed to provide at least a qualitative evaluation of food value for other animals as well.

Therefore, contact times of at least about 10 minutes, preferably at least about 30 minutes, are employed in the methods of this invention. Even longer contact times are preferred for the treatment of relatively refractory cellulosic materials, such as accumulated wood scraps and cardboard, and for the treatment of some types of in situ vegetation, such as crop stubble and vines, when it is desired to significantly weaken the physical structure of the cellulosic material. The urea-sulfuric acid components employed in the methods of this invention remain active indefinitely unless they are diluted or washed away with excessive amounts of water or other solvents or are neutralized with base. Thus, contact times of indefinite duration can be used, although contact times of up to 48 hours are sufficient to effect significant improvements in accordance with all embodiments of this invention. I have also found that the urea-sulfuric components, in addition to directly modifying cellulosic materials, also accentuate the enzymatic activity of bacteria which gradually degrade the physical structure of cellulosic materials such as crop stubble, vines, and accumulated cellulosic wastes. Thus, significant weakening of such cellulosic materials can be achieved by treating them with very minor amounts, i.e., 0.1 weight percent, of the urea-sulfuric acid component (based on the water-free weight of urea and sulfuric acid), and allowing the treated material to stand for a month or more prior to use or further processing.

The urea-sulfuric acid component can be allowed to remain in the treated cellulosic material, it can be extracted by washing with water, or it can be neutralized with base, such as the oxides or hydroxides of the alkali or alkaline earth metals. Other bases are also suitable for neutralizing the sulfuric acid contained in the urea-sulfuric acid component. Such neutralization may be preferable in the treatment of certain cellulosic materials, particularly in the preparation of cellulosic materials which are to be used as food products, or as components of food products, for humans, ruminants, or other animals.

The novel compositions of this invention involve (1) mixtures of cellulosic materials and the urea-sulfuric acid components useful in the methods of this invention, which compositions may optionally contain the described surfactants, and (2) modified cellulosic materials resulting from the treatment of cellulosic materials in accordance with the methods of this invention. In particular, the novel compositions of this invention involve cellulosic compositions which have been modified and/or physically weakened, or in which the food value has been increased, by reaction of the cellulosic material with the described urea-sulfuric acid components. The concentration of the urea-sulfuric acid components in the novel compositions should be sufficient to modify the cellulosic material. Such concentrations will usually correspond to at least about 0.1 weight percent of the combination of urea and sulfuric acid based on the weight of cellulosic material; generally they correspond to at least about 1, and preferably at least about 2 or more pounds of the urea-sulfuric acid component (based on the combined weight of urea and sulfuric acid) per 100 pounds of cellulosic material. The urea-sulfuric acid component may be retained in the novel cellulosic compositions of this invention as such, or it can be removed by washing with water or other solvents as described above. In the alternative, the urea-sulfuric acid component can be neutralized with base as descbribed above, in which case the novel cellulosic composition would contain urea and the neutralization products of sulfuric acid. Such compositions contain added nutrient value derived from the urea and neutralized sulfuric acid, and are particularly suitable for use as ruminant feeds.

The methods and compositions of this invention have numerous advantages over methods and compositions employed in the modification of cellulosic materials available to the art. They can be employed to chemically modify cellulosic materials, and particularly to physically weaken cellulosic materials and/or to increase the food value of such materials even at ambient conditions. The methods and compositions of this invention do not introduce any toxic materials into the treated cellulosic material or the environment, and they are relatively nontoxic to applicators and processing personnel.

The urea-sulfuric acid components introduce only animal and plant nutrients into the treated cellulosic material and/or the environment. The novel methods and compositions do not destroy any food value or other commercial value of cellulosic material, and they are more efficient than is the use of sulfuric acid or other known procedures since the urea-sulfuric acid components are not consumed by reaction with the cellulosic component (although they may be neutralized by other components contained in some cellulosic materials.) Since the methods and compositions of this invention may be used to markedly reduce the physical strength of cellulosic materials, even at relatively low dosage rates, they facilitate clearing land of underbrush, removing crop residues from agricultural lands, cultivation of agricultural lands, harvesting of certain food crops (particularly tuberous crops such as potatoes, beets, and the like), and the production of cellulosic materials which are for the manufacture of cellulose-containing articles such as craft paper, particle board, and other cellulosic products, and they reduce the costs of such treatments.

The methods and compositions however can even be employed to convert cellulose to glucose by contacting the cellulosic material with a sufficient amount of the urea-sulfuric acid component and for a sufficient period of time to allow the hydrolysis of the cellulosic feed material to become complete.

The invention is further described by the following examples which are illustrative of specific modes of practicing the invention and are not intended as limiting the scope of the invention as defined by the appended claims:

EXAMPLE I

Irish potato vines are topically treated prior to harvest with a urea sulfuric acid component in accordance with this invention having the composition 17-0-0-17 applied at a rate of 15 gallons per acre diluted with four gallons of water per gallon of the 17-0-0-17 formulation to facilitate pre-harvest cleanup, minimize interference of topical vegetation with the harvesting effort, and accelerate senescence of the tubers. Complete wilting and necrosis of vegetation is evident within 4 hours at which time the physical strength of the crop vines has been reduced to the point that they can be easily parted by potato harvesting equipment. Within 72 hours, the tubers have senesced to the point that their skins are characteristically thicker and are sufficiently strong to resist scarring and peeling by harvesting and handling equipment. Potatoes harvested in the same field at the same time which are not treated prior to harvest by the described procedure have thin, friable peels characteristic of "new" potatoes.

EXAMPLE II

Tomato vines are treated post-harvest to facilitate cleanup of the crop stubble by topical application of 40 gallons per acre of the 17-0-0-17 composition diluted to 200 to 1 with water. This dilution provides sufficient spray volume to spray the foliage approximately to the point of runoff.

This treatment is sufficient to completely wilt and significantly reduce the physical strength of the tomato foliage and vines within two to four hours and to markedly reduce the vines' resistance to cultivation tilling equipment.

EXAMPLE III

Rice stubble remaining after harvest is treated by topical application of 30 gallons per acre of the 17-0-0-17 composition diluted with four volumes of water per volume of 17-0-0-17. Within 48 hours, the physical strength of the in situ stubble is reduced sufficiently so that it can be easily crumbled by hand.

EXAMPLE IV

The ruminant food value of harvested, dry rice stubble is increased by treatment with the urea-sulfuric acid component having the composition 17-0-0-17 at a dosage rate of 10 pounds of 17-0-0-17 per 100 pounds of dried rice stubble. The 17-0-0-17 is diluted with 3 volumes of water per volume of 17-0-0-17 to provide adequate mixing with the rice stubble, and the mixture is held at 60° F. for 48 hours before use.

EXAMPLE V

The digestibility of celery by humans is increased by treating undried harvested celery with the urea-sulfuric acid component having the composition 17-0-0-17 at a dosage rate of 5 pounds of 17-0-0-17 per 100 pounds of celery. The 17-0-0-17 is diluted with 5 volumes of water per volume of 17-0-0-17 to allow adequate distribution of the urea-sulfuric acid component throughout the celery and the resulting mixture is held at 70° F. for 24 hours before use.

EXAMPLE VI

Sawdust is partially hydrolyzed and is physically weakened by contact with 10 pounds of the urea-sulfuric acid component having the composition 18-0-0-17 containing 2 weight percent Thompson-Hayward's T-MULZ 891-brand surfactant per 100 pounds of sawdust. The 18-0-0-17 is diluted with 4 volumes of water per volume of 18-0-0-17 to provide adequate contact of the urea-sulfuric acid component with the sawdust and the mixture is held at 100° F. for 48 hours. The mixture can then be neutralized by the addition of sodium hydroxide and water washed to remove residual urea and sodium sulfate. The treated sawdust can be employed as a ruminant feed supplement or as a precursor for the manufacture of craft paper.

EXAMPLE VII

The physical strength of finely divided waste newspaper is reduced and its compressibility is increased by contact with 2 pounds of the urea-sulfuric acid component having the formulation 17-0-0-17 containing 2 weight percent (based on the weight of 17-0-0-17) of Thompson-Hayward's T-MULZ 891-brand surfactant per 100 pounds of newspaper. The 17-0-0-17 is diluted with 3 volumes of water per volume of 17-0-0-17 to provide sufficient fluid volume to evenly spray the urea-sulfuric acid component onto the finely divided newspaper, and the resulting combination is held at a temperature of 70° F. for 48 hours. The resulting physically weakened newspaper is then be baled for storage or shipment or can be used directly as a precursor in the manufacture of craft paper.

While particular embodiments of the invention have been described, it will be understood, of course, that the invention is not limited thereto since many obvious modifications can be made and it is intended to include within this invention any such modifications as will fall within the scope of the appended claims.

Having described my invention, I claim:

1. The composition of matter comprising cellulosic material and the monourea adduct of sulfuric acid.

2. The composition defined in claim 1 free of decomposition products of urea or sulfuric acid.

3. The composition defined in claim 1 comprising a surfactant.

4. The composition defined in claim 1 comprising an amount of said monourea adduct of sulfuric acid sufficient to weaken the physical structure of said cellulosic material.

5. The composition defined in claim 1 comprising an amount of said monourea adduct of sulfuric acid sufficient to increase the food value of said cellulosic material.

6. The composition defined in claim 1 wherein said cellulosic material comprises vegetable protein.

7. The composition defined in claim 1 comprising at least about 1 pound of said monourea adduct of sulfuric acid per 100 pounds of said cellulosic material.

8. The composition defined in claim 1 wherein said cellulosic material comprises harvested plant matter.

9. The composition defined in claim 1 wherein said cellulosic material comprises cellulosic matter other than plant matter.

10. The composition defined in claim 1 wherein said cellulosic material comprises a member selected from the group consisting of paper, wood scrap, and combinations thereof.

11. The composition defined in claim 1 free of unadducted sulfuric acid.

12. A composition of matter comprising the reaction product of cellulosic material and the monourea adduct of sulfuric acid.

13. The composition defined in claim 12 wherein said urea and sulfuric acid, in combination, constitute at least about 0.1 weight percent of said composition based on the weight of said cellulosic material.

14. The composition defined in claim 12 wherein said molar ratio of said urea to said sulfuric acid is within the range of about ½ to about 3/2.

15. The composition defined in claim 12 free of decomposition products of urea or sulfuric acid.

16. The composition defined in claim 12 comprising a surfactant.

17. The composition defined in claim 12 comprising a sufficient amount of said combination of said urea and sulfuric acid to physically weaken said cellulosic material.

18. The composition defined in claim 12 wherein the concentration of said combination of said urea and sulfuric acid is sufficient to increase the food value of said cellulosic material.

19. The composition defined in claim 12 wherein said cellulosic material comprises vegetable protein.

20. The composition defined in claim 12 comprising at least about 1 pound of said combination of said urea and sulfuric acid per 100 pounds of said cellulosic material.

21. The composition defined in claim 12 wherein said cellulosic material comprises harvested plant matter.

22. The composition defined in claim 12 wherein said cellulosic material comprises cellulosic matter other than plant matter.

23. The composition defined in claim 12 wherein said cellulosic material comprises a member selected from the group consisting of paper, wood scrap, and combinations thereof.

24. The composition defined in claim 12 free of unadducted sulfuric acid.

25. A composition of matter comprising cellulosic material selected from the group consisting of harvested plant matter, non-plant matter, and combinations thereof, and the monourea adduct of sulfuric acid.

26. The composition defined in claim 25 wherein the concentration of said monourea adduct of sulfuric acid is sufficient to weaken the physical structure of said cellulosic material.

27. The composition defined in claim 25 wherein the concentration of said monourea adduct of sulfuric acid is sufficient to increase the food value of said cellulosic material.

28. The composition defined in claim 25 free of unadducted sulfuric acid.

29. A composition formed by admixing a composition comprising the monourea adduct of sulfuric acid and cellulosic matter selected from the group consisting of harvested plant matter, cellulosic matter other than plant matter, and combinations thereof.

30. The composition defined in claim 29, wherein said cellulosic matter comprises harvested plant matter.

31. The composition defined in claim 29 comprising at least about 1 pound of said monourea adduct of sulfuric acid per 100 pounds of said cellulosic matter.

32. The composition defined in claim 31, wherein said cellulosic matter is selected from the group consisting of harvested plant matter, paper, woodscrap, and combinations thereof.

33. The composition defined in claim 29 comprising at least about 2 pounds of said monourea adduct of sulfuric acid per 100 pounds of said cellulosic matter.

* * * * *